United States Patent [19]

Menyhert

[11] 4,057,524

[45] Nov. 8, 1977

[54] EPOXY DERIVATIVE COMPOSITIONS

[76] Inventor: William R. Menyhert, Rte. 1 Box 97, Easton, Md. 21601

[21] Appl. No.: 654,720

[22] Filed: Feb. 2, 1976

Related U.S. Application Data

[63] Continuation-in-part of Ser. No. 456,238, March 29, 1974, abandoned.

[51] Int. Cl.$^2$ ............................................. C08L 33/02
[52] U.S. Cl. ..................... 260/29.2 EP; 260/29.6 NR; 260/29.6 R; 260/837 R
[58] Field of Search .................. 260/29.6 WR, 29.6 R, 260/29.2 EP, 837

[56] References Cited

U.S. PATENT DOCUMENTS

| | | | |
|---|---|---|---|
| 2,795,564 | 6/1957 | Conn et al. .................. | 260/29.6 TA |
| 2,954,358 | 9/1960 | Hurwitz ........................ | 260/29.6 NR |
| 3,238,170 | 3/1966 | Wolff et al. ............................ | 260/836 |
| 3,288,883 | 11/1966 | Temin et al. ................. | 260/29.6 NR |
| 3,331,886 | 7/1967 | Zimmerman et al. ................ | 260/835 |
| 3,390,114 | 6/1968 | Uhl et al. ............................... | 260/836 |
| 3,423,345 | 1/1969 | Hsu et al. .......................... | 260/18 EP |
| 3,563,929 | 2/1971 | Guldenpfennig ............ | 260/29.6 NR |
| 3,699,079 | 10/1972 | Haynes ............................. | 260/47 EP |
| 3,806,483 | 4/1974 | Juba et al. ..................... | 260/29.6 NR |
| 3,812,615 | 5/1974 | Jamison ......................... | 260/17.4 CL |

FOREIGN PATENT DOCUMENTS

| | | | |
|---|---|---|---|
| 848,350 | 9/1960 | United Kingdom ........ | 260/29.6 NR |

OTHER PUBLICATIONS

Paquin, *Epoxydverbindungen und Epoxydharze*, Springer-Verlag, Berlin, 1958.

*Primary Examiner* — M. J. Welsh
*Attorney, Agent, or Firm* — DePaoli & O'Brien

[57] ABSTRACT

Process for producing a new class of epoxy derivative compositions involving the steps of equalizing the reactivity rate of the alpha and beta carbon atoms of an epoxy group of an epoxy containing compound by contacting said compound with carbon dioxide to generate resonance of the oxirane oxygen thereby to stabilize the velocity of the subsequent primary reaction of the compound, and passing the stabilized epoxy compound into a aqueous liquid system. The liquid system can include a dispersion of at least one other compound including a group reactive with the epoxy containing compound. According to a preferred form of the invention, an epoxy resin is passed into a reaction zone and into contact with a carbon dioxide layer to generate resonance of the oxirane oxygens of the epoxy groups of said resin. The stabilized epoxy resin is then passed directly from said carbon dioxide layer into a single liquid phase aqueous dispersion of a polymer of an acrylic ester, such for example as of acrylic or methacrylic acid including pendant groups (e.g., carboxyl or hydroxyl) reactive with the epoxide. Addition of the epoxy to the acrylic dispersion is accompanied by stirring until addition is complete. The resulting single liquid phase epoxy dispersion is characterized by excellent shelf life, and is suitable as a coating material, plasticizer, base material for chemical manufacture, and in the manufacture of polymer fibers. As a coating material, when applied to a substrate and air dried, the epoxy derivative-acrylic polymer dispersion produces a tough, flexible film having outstanding properties including thermoplastic memory characteristics.

32 Claims, 1 Drawing Figure

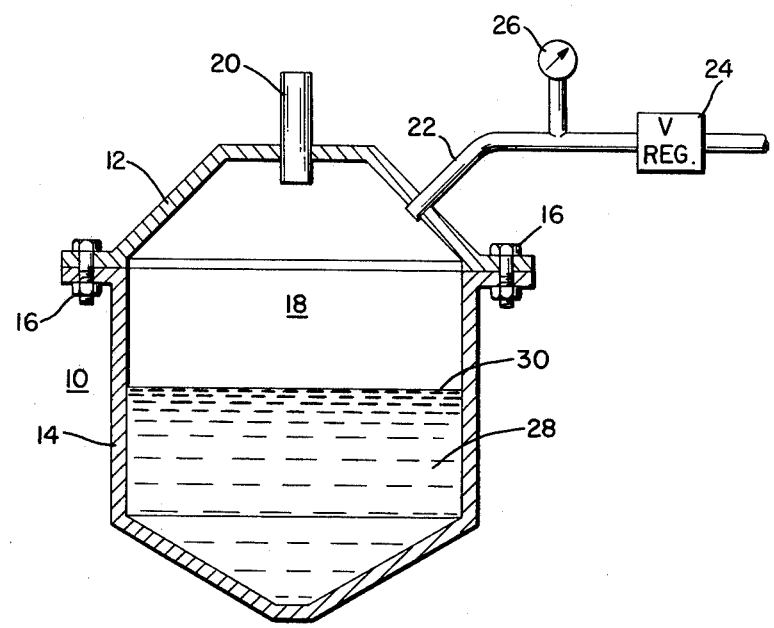

EPOXY DERIVATIVE COMPOSITIONS

CROSS REFERENCE TO RELATED APPLICATION

This application is a continuation-in-part of copending application Ser. No. 456,238, filed Mar. 29, 1974 and now abandoned.

BACKGROUND OF THE INVENTION

1. Field of the Invention

This invention relates to the production of a new class of epoxy derivative compositions and, more particularly, is concerned with a process for equalizing the reactivity rate between the alpha and beta carbons of a terminal epoxy group of an epoxy-containing compound to alter the reactivity of said epoxy-containing compound in an aqueous system. The invention also contemplates the production of stable, film-forming aqueous dispersions of a mixture of an epoxy containing compound and an acrylic polymer including a group reactive with the epoxy compound. Such mixtures, upon drying in air, provide tough, flexible compositions having thermoplastic memory and other desirable physical characteristics.

2. Description of the Prior Art

Aqueous dispersions of epoxy resins are well known, commercially available materials having wide applicability in the coating field. Generally speaking, such aqueous dispersion systems of epoxy resins are sold as two separate components. Prior to use, the two components are admixed, and must be used before the combined mix cures into an isoluble, infusible mass. Thus, aqueous, epoxy-based single component coating compositions characterized by extended shelf life have simply been unavailable in the prior art.

Water based acrylic polymer dispersions for use in coating applications and as paints are also known. See, e.g., U.S. Pat. No. 2,795,564 - Conn et al. The resulting coatings produced from such acrylic dispersions generally have good color and color retention and satisfactory resistance to water-borne stains, as well as possess other desirable properties. In general, such acrylic dispersions have found utility as water-based paints and are well known, commercially available materials made for that purpose.

While numerous attempts have been made in an effort to combine the desirable characteristics of epoxy resins with the desirable characteristics of acrylate esters (see e.g., U.S. Pat. Nos. 3,238,170 - Wolf et al; 3,288,884 - Sonnabend et al; 3,291,857 - Howerton; 3,390,114 - Uhl; 3,418,392 - Leitner; 3,466,347 - David; 3,513,222 - Speitel; 3,519,702 - Wear; 3,563,929 - Guldenpfennig; and 3,657,381 - Speitel) no single component, aqueous dispersion of a combination of epoxy and acrylate polymer mixtures having extended shelf life characteristics have heretofore been prepared in the prior art.

In studies of active sites of epoxy compounds by crystal X-ray microscopy, it was found that the oxirane oxygen is bound to the beta carbon in a shorter bond than to the alpha carbon:

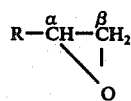

where R is a hydrocarbon radical. Investigators have learned that the reactivity of the above epoxy configuration in aqueous media will be such that the primary reaction always involves the beta carbon atom:

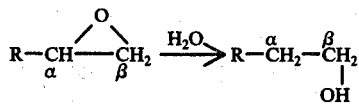

See W. C. J. Ross, 1950 *Journal of Chemical Society*, London, Eng. pp. 2257–2272; A. J. Durbetaki, *Analytical Chemistry*, Vol. 28 No. 12, December 1956, pp. 2000–2001; *Analytical Chemistry*, Vol. 30 No. 12, December 1958, pp. 2024, 2025; B. D. Sully, *Analyst*, Vol. 85, December 1960, pp. 895–897; R. R. Jay, *Analytical Chemistry*, Vol. 36 No. 3, March 1964, pp. 667–668; G. A. Stenmark, *Analytical Chemistry*, Vol. 29 No. 9, September 1957, pp. 1367–1369.

Where, as may be the case in aqueous acrylic dispersion systems, contaminating ionic material, such as free halides, are present, the secondary reaction of the epoxy derivative compound resulting from the primary reaction will involve a salinification, i.e., the free halide will attach to the alpha carbon atom, and the further activity of the epoxy-derivative group is inhibited completely. As a consequence, it has not been possible to provide stable, epoxy-acrylic dispersion systems.

DESCRIPTION OF THE INVENTION

Having in mind the limitations of the prior art, it is a primary object of the invention to provide a new class of epoxy derivative compositions by a process which includes equalizing the reactivity rates of the alpha and beta carbon atoms of an epoxy group of an epoxy-containing compound.

Another object of the invention is to provide aqueous dispersions of one or more epoxy containing compounds and acrylics which, upon drying in air, provide tough, flexible compositions having thermoplastic memory as well as other desirable physical characteristics.

Briefly stated, the foregoing and other objects of the invention may be attained by a process for stabilizing the velocity of the primary reaction of an epoxide having at least one oxirane group in an aqueous system which process comprises passing the epoxide into a reaction zone including an aqueous liquid and carbon dioxide for generating resonance of the oxirane oxygen of said epoxide when it contacts said carbon dioxide, contacting the epoxide with the carbon dioxide to stabilize said epoxide, and passing the said stabilized epoxide into said aqueous liquid.

In accordance with a preferred form of the invention, an epoxy resin including terminal epoxy groups is passed through carbon dioxide, to generate resonance of the oxirane oxygens of the epoxide, and the epoxide is then passed directly into an aqueous system. The subsequent primary reaction of the stabilized epoxide in the aqueous system will conform to the equation:

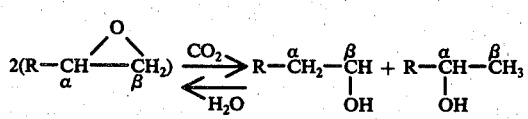

where R is a hydrocarbon radical.

As a result of equalizing the reactivity rate of the alpha and beta carbon atoms of the epoxy ring, the subsequent primary reaction of the epoxide in the aqueous system is such that approximately half of the resulting product of the primary reaction is a primary alcohol and approximately half of the product of the primary reaction is a secondary alcohol. The tendency for the undesired secondary reaction to result in salinification by addition of a halogen at the alpha carbon is thus substantially diminished.

In accordance with the invention, an epoxy compound, or mixture of two or more different epoxy compounds, is passed through the gaseous layer or blanket of carbon dioxide which generates resonance of the oxirane oxygen. The aqueous system into which the epoxy compound is passed may be acid or basic, and preferably will have a pH ranging from about 4 to about 9.5, although lower and higher pH values may also be used. In general, the solids content of the epoxy dispersion may range from 1% to 90%, and preferably from 1% to 40%. Addition may be accomplished at ambient room temperatures. Temperatures in the range of from 4° C. to about 41° C. are preferred, although lower and higher temperatures may be used.

The rate of the addition of the epoxy resin into the reaction zone including the carbon dioxide layer may also vary within wide limits. Generally, it is preferred to add the epoxy resin in the form of an aqueous dispersion to the reaction zone slowly as for example in a drop-by-drop fashion, with smaller drops being preferred, to maximize the area of gas-liquid interface between the epoxy dispersion and the carbon dioxide. Thus, the epoxy dispersion may be introduced into the reaction zone containing the carbon dioxide in the form of a fine mist or spray which then passes, by action of gravity, through the carbon dioxide layer and directly into an interfacial zone which is part of the aqueous liquid system that is located below the carbon dioxide layer.

The pressure of the carbon dioxide in the reaction zone may also vary within wide limits, but preferably should be above one atmosphere and may range as high as twenty atmospheres or above, depending upon the type of equipment that is available for use. Generally speaking, higher pressures will cause faster resonance rates, and hence higher reaction rates, and can be employed provided that the temperature of the reaction mixture is kept below about 40° C.

In accordance with the invention, the aqueous-epoxide dispersion, which as noted above may include a single epoxy resin or a mixture of two or more different epoxy resins, is passed through the gaseous layer or blanket of carbon dioxide which generates resonance of the oxirane oxygen of the epoxy groups of the epoxide, and is then passed into an aqueous system. To minimize unnecessary side reactions, deionized water should be used in the preparation of both the epoxy aqueous dispersion as well as the aqueous system into which the activated epoxide is passed after it contacts the carbon dioxide layer. The aqueous mixture into which the epoxy resin dispersion is passed in accordance with the invention may contain the compound, or mixture of compounds, with which the activated epoxide can interact to provide the new epoxy derivative compositions of the inventions.

Among the materials which can be interacted with the stablized epoxide resin in accordance with this invention are the fatty acids, steroids, ethylenically unsaturated compounds such as polyvinyl chloride and polyvinyl acetate, urea and its derivatives, polyurethanes, and derivatives of acrylic and methacrylic acids and esters thereof, hereinafter referred to as "acrylates", which are reactive with the epoxy resin. Other monomeric and polymeric materials which may be combined with the stablized epoxide in accordance with the present invention will readily occur to those skilled in the art.

The epoxy-derivative compositions of this invention may be formulated with varying proportions of each component, depending upon the properties desired. Thus, where epoxy-acrylate compositions are contemplated, the epoxy component (which may comprise a mixture of two or more different epoxy materials) may be used in proportions ranging from about 0.1% to as much as 50% of the total weight of the epoxy-acrylate solids in the mixture. Generally speaking, where aqueous dispersions of the epoxy derivative compositions of the invention are desired for coating applications, it has been found that the acrylate to epoxy proportions should preferably vary so that two or more parts by weight of the acrylate component (or mixture of two or more acrylate components) are reacted with one or less parts by weight of the epoxy component (or mixture of two or more epoxy components).

The proportions referred to above are based upon the total weight of resin solids in the composition.

The epoxy resins or epoxides useful in the practice of the present invention are organic compounds which contain at least one oxirane group. A typical epoxy resin which can be used in the practice of the invention is one containing terminal epoxy groups. Representative of this class are the complex polymeric reaction products of an epihalohydrin such as epichlorohydrin and a phenol having at least two phenolic hydroxy groups such as bis-(4-hydroxyphenyl)-2,2 propane. U.S. Pat. Nos. 2,495,295 to Greenlee, 2,500,600 to Bradley, and 2,511,913 to Greenlee, describe such epoxy materials. The epoxy resins used therein have more than one epoxy group per molecule and may be obtained by reacting a polyol (e.g., a polyhydric alcohol or phenol) such as hydroquinone, resorcinol, glycerine, condensation products of phenols with ketone, such as, for example, bis-(4-hydroxyphenyl)2,2 propane with epichlorohydrin. The reaction between the epihalohydrin and the dihydric phenol or dihydric alcohol is generally carried out in the presence of caustic alkali which is usually employed in excess but in at least the quantity necessary to combine with the halide liberated from the halohydrin. The products obtained may contain terminal epoxy groups or terminal epoxy groups and terminal primary hydroxyl groups. In the complex reaction mixture, the terminal epoxy groups are generally in excess of the terminal primary hydroxyl groups. The molecular weight of the epoxy resins may be controlled by the relative proportions of the reactants as well as by the extent to which the reaction is carried on.

The typical commercial epoxy resins sold for example under the name of "Epon" by Shell Chemical Corporation, under the name "Araldite" by the Ciba Company, as "Epi-Rez" resins by Devoe-Reynolds Company, and "ERL Resins" by the Bakelite Company are mixtures of polymers, the major component of the resin being the polyglycidyl ethers of polyhydric phenols such as bisphenol-A, and epichlorohydrin. By using an excess of epichlorohydrin, the lower molecular weight liquid polymers are formed, and with higher proportions of bisphenol higher molecular wieght solid resins result.

A typical epoxy resin consists of 60% by weight of an epoxide having the structure:

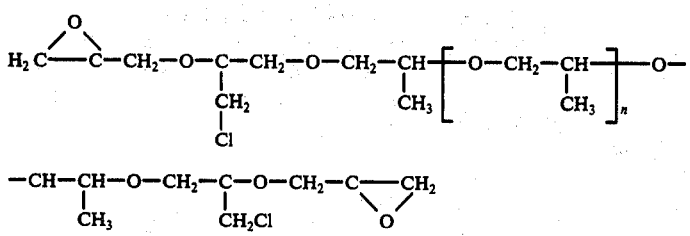

where n has a value from 1 to 20.
and 40% by weight of an epoxide having the structure:

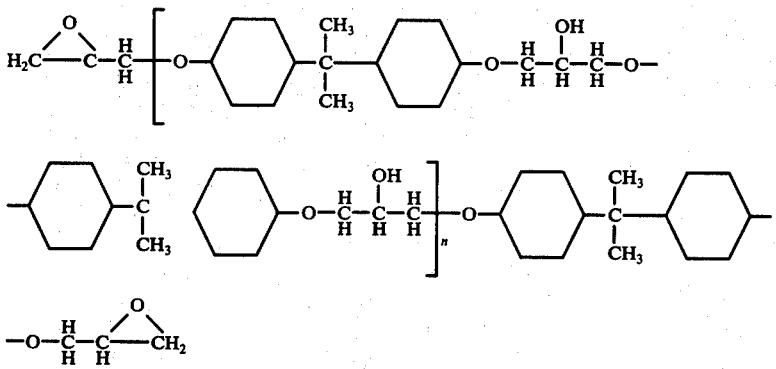

where $n$ has a value from 1 to 20.

According to a preferred form of the invention, a new and significantly improved class of epoxy-derivative acrylate compositions may be prepared which have been found to possess properties rendering them eminently suitable in a variety of applications, and particularly in coating applications. Among the acrylic materials suitable for use in production of epoxy-derivative compositions of the invention are the monomeric and polymeric alpha, beta unsaturated, monovinylidene carboxylic acids, or other alpha-substituted, polymerizable acrylic acid compounds reactive with the epoxy resin. Methacrylic and acrylic acids are preferred. In place of the free acids, the water soluble salts may be used, including the alkali metal salts such as lithium and potassium carboxylates. The salts may be pre-formed or may be formed in the aqueous dispersion system upon adjustment to the desired pH prior to the introduction of the stabilized epoxy.

Another class of acrylic materials useful in the invention are the primary and secondary alkyl acrylates, with alkyl constituents up to 18 carbon atoms, primary or secondary alkyl methacrylates with alkyl substituents of 5 to 18 or more carbon atoms, including at least one pendant group reactive with the epoxy resin, such as, for example, hydroxyl, carboxyl, amino, amido, cyanato, etc. groups. Further examples of groups reactive with the oxirane ring of the epoxide are set forth in Lee and Neville, *Handbook of Epoxy Resins,* 2d. ed. (1967), particularly at pp. 5-32 to 5-39, whose disclosure, by reference herein, is incorporated and made part of the disclosure and teaching of the present invention.

The preferred monovinylidene compounds are the acrylates and methacrylates noted above, and particularly esters reactive with the epoxide and having alkyl groups including not more than 12 carbon atoms. The acrylic materials useful in the practice of the invention also include the polymers of the above monomers which are reactive with the epoxide with which they are to be combined. A particularly preferred class of polymers may be prepared from monomers represented by the formula:

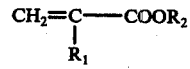

where $R_1$ is hydrogen or the methyl group and $R_2$ is, when $R_1$ is methyl, a primary or secondary alkyl group of 5 to 18 carbon atoms including a substituent group reactive with the epoxide, or where $R_1$ is hydrogen, an alkyl group of not over 18 carbon atoms, preferably of from 2 to 12 carbon atoms, including a substituent group reactive with the epoxide. Examples of compounds falling within the scope of the above formula are hydroxyethyl acrylate, carboxybutyl acrylate, hydroxyisobutyl acrylate, hydroxyethyl methacrylate, 2-aminobutyl methacrylate, carboxypropyl methacrylate, and 3,5-diaminohexyl methacrylate.

Yet another class of useful monomers are those corresponding to the formula:

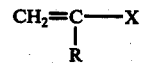

where R is a hydrogen or the methyl group and wherein X represents one of the groups —CN, and ester-forming groups —COOR, wherein R is a substituted cyclohexyl group including a substituent reactive with the epoxide.

A preferred class of acrylic materials useful in the practice of the invention are the aqueous dispersions of acrylic and methacrylic interpolymers such as described in U.S. Pat. No. 2,795,564 whose disclosure, by reference herein, is incorporated and made a part of the teaching of the present invention.

Examples of specific acrylic materials which may be used to provide the epoxy derivative compositions of the invention include (a) aqueous dispersions of an interpolymer of ethyl acrylate, methyl methacrylate, and methacrylic acid, (b) colloidal dispersions including mixtures of 80% by weight of acid soluble methyl methacrylate, 5% polymethyl methacrylate including pendant hydroxyl or carboxyl groups, 10% of either polyethyl or polybutyl methacrylate including pendant hydroxyl or carboxyl groups and 5% of either isopropyl or isobutyl methacrylate including pendant hydroxyl or carboxyl groups, and (c) a water solublized colloidal dispersion of polymethyl methacrylate (including pendant hydroxyl or carboxyl groups) in an alcohol, such as tert-butanol, isopropanol, ethanol or mixtures thereof. Typical examples of such commercially available acrylic materials are Rhoplex SS-521, Rhoplex AC-388, Acrysol WS-12, Acrysol WS-24, Acrysol WS-32, and Acrysol WS-50, all marketed by the Rohm & Haas Company. Other suitable acrylic dispersion mixtures will readily occur to those skilled in the art.

DESCRIPTION OF THE DRAWING AND PREFERRED EMBODIMENTS

For further objects and advantages of the invention and a more detailed discussions of preferred embodiments thereof, reference is to be had to the following detailed description taken in conjunction with the accompanying drawing which is a cross-section view of apparatus useful in the practice of one form of the invention.

As shown in the drawing, a hollow pressure vessel 10 is provided with a removable cover or roof 12 which is secured to the lower reactor portion 14 by suitable means, such as screw bolts 16 to provide a gas-tight reaction zone 18. The roof 12 includes suitable opening means 20 for adding materials to the reaction zone 18 and to permit introduction of suitable stirring means (not shown) as well as pH and temperature measuring means (not shown). Cover 12 is also provided with a gas delivery means 22 including flow connections and pressure regulator or relief means 24 for regulation and relief of the pressure in the vessel 10 which pressure may be observed by a suitable pressure regulator gauge 26.

In accordance with a preferred form of the invention, as more specifically described in the examples which follow, the reactor vessel 14 is filled to the desired level with a quantity of an aqueous dispersion of the desired acrylic polymer, the dispersion having its pH adjusted so that it is between 4.0 and 9.0. The space above the aqueous dispersion 28 is next purged with carbon dioxide gas such that the entire air space volume above the level 30 of the liquid layer 28 is filled with carbon dioxide whose pressure is maintained at at least one atmosphere. In accordance with the invention, the aqueous epoxy dispersion is passed into the reaction zone 18 via opening means 20 such that the dispersion first passes through and is in intimate contact with the carbon dioxide gas in the space above the acrylic dispersion 28. The epoxy dispersion is thus permitted to pass through the $CO_2$ layer, which is supported by and in intimate contact with the surface 30 of the acrylate dispersion 28. The epoxy material, after contacting the $CO_2$ layer, is passed directly into the aqueous dispersion of acrylic polymer 28. Addition of the epoxide material to the reaction zone is accompanied by continuous stirring of the reaction mixture formed by adding the epoxy dispersion to the acrylic dispersion layer 28. The temperature of the reaction mix is maintained within the range of 4° C. to 40° C., and preferably within the range of 20° to 26° C. throughout the addition of the epoxide to the acrylic dispersion.

In order that those skilled in the art may better understand how the present invention may be practiced, the following examples are offered by way of illustration and not by way of limitation. All parts and percentages are by weight unless otherwise noted.

EXAMPLE 1

An epoxy resin dispersion was prepared in the following manner: To a mixing vessel such as shown in the drawing, which had been purged with carbon dioxide, were added 17.6 lbs. of Ciba Araldite 509 (a liquid epoxy resin which is the diglyicdyl ether of bisphenol-A diluted with decyl glycidyl ether and 8.8 lbs. of Ciba Araldite 6010 (a liquid diglycidyl ether of bisphenol-A). The epoxy mixture was mixed in the reaction vessel under a pressure of 50 PSIG of carbon dioxide for approximately 5 minutes. The pressure was then removed and 222.4 grams of a detergent (Ivory soap granules) were added to the reaction vessel followed by the addition of 2,360 milliliteres of water and 6.2 lbs. of butyl Cellosolve. The pressure of the carbon dioxide in the vessel was then increased to 100 PSIG and the contents of the vessel were stirred for about 1 hour under a $CO_2$ pressure of from 80 to 100 PSIG. The pressure was then released and one gallon of material was drained from the bottom of the vessel and poured back into the top. The pressure was reapplied and mixing was continued at 100 PSIG for approximately another hour. Mixing was discontinued and the $CO_2$ was retained in the vessel under pressure for approximately 12 hours. At the end of that period, the pressure in the vessel was found to drop to 35 PSIG. The pressure was released and the product removed and poured into a seperatory funnel. The aqueous phase was discarded and the organic, resin-containing phase was used to provide the epoxy derivative compositions as described below.

One hundred twenty parts by weight of a water base acrylic resin colloidal sol (Rohm & Haas WS-12) were charged to a reaction vessel as shown in the drawing. Mixing of the acrylic material was then commenced and carbon dioxide was added to the reaction vessel to create a gas blanket over the acrylic mix and fill the air space above the surface of the acrylic material. Sixty parts by weight of water were then added to the reaction vessel. Next, 30 parts by weight of the epoxy resin as prepared above were added to the reaction vessel including the acrylic mix blanketed by the carbon dioxide layer such that the epoxy resin was passed slowly through the layer of carbon dioxide and into the acrylic mix. Sixty-six parts of AC-61 (Rohm & Haas acrylic emulsion), followed by 120 parts of a premix consisting of 86% SS-521 (Rohm & Haas acrylic emulsion), 4.3% butyl Cellosolve and 9.7% water were then added to the reaction vessel with stirring. The carbon dioxide gas flow was stopped after all ingredients were added to the vessel and mixing of the ingredients was continued for 25 minutes. The temperature of the mixture was maintained below 75° F. throughout the mixing operation. The batch was then ready for storage for use and contained a dispersion of 36% solids (30% derived from the acrylic mix and 6% derived from the epoxy mix). The mix had a pH of approximately 8. When applied to substrates and dried in air, a clear, flexible coating was obtained having properties such as those more fully discussed below.

EXAMPLE 2

Three hundred sixty parts of Rohm & Haas B-72 acrylic solution was added to a reaction vessel as shown in the drawing. Mixing was commenced and carbon dioxide was passed into the reaction vessel to create the gas blanket and to fill the air space above the acrylic solution. Sixty parts by weight of the epoxy mix as prepared in Example 1 were then added to the reaction vessel slowly such that the epoxy passes first through the carbon dioxide layer before contacting the liquid acrylic mix. Mixing was continued throughout the addition of the epoxy so that fresh acrylic mix was exposed to the carbon dioxide gas phase interface throughout the mixing operation. One hundred thirty parts by weight of water were then added to the mixture. The $CO_2$ gas flow was then stopped and mixing was continued for approximately 20 minutes. The resulting product had a pH of approximately 7. When applied to substrates and dried in air, a clear, flexible coating was obtained.

EXAMPLE 3

An epoxy resin dispersion was prepared in accordance with the method set forth in Example 1 except that 48 lbs. of a solution of a solid epoxy resin (Ciba Araldite 7097) in butyl Cellosolve was substituted for the mixture of Araldite 509 and Araldite 6010 used in Example 1, and the addition of 6.2 pounds of butyl Cellosolve was omitted. The resulting epoxy dispersion was used in the preparation of the epoxy derivative composition as set forth in this Example.

To the reaction vessel as shown in the drawing were added 320 parts of Rohm & Haas N-495 acrylic emulsion. Mixing was commenced and the carbon dioxide was added to the reaction vessel to create the gas blanket and fill the air space over the acrylic emulsion. Two hundred forty parts of water were added to the reaction vessel followed by the addition of 40 parts by weight of the epoxy dispersion whose preparation is described above in this Example. The $CO_2$ gas flow to the reaction vessel was stopped after addition of all of the ingredients to the reaction vessel was completed. Mixing was continued for 30 minutes. The resulting product had a pH of approximately 4. When applied to substrates and dried in air, a clear, flexible coating was obtained.

EXAMPLE 4

Example 3 was repeated except that the epoxy resin dispersion of Example 1 was used in lieu of the epoxy resin dispersion whose preparation is described in Example 3. The resulting product had a pH of approximately 4, and when applied to a substrate and dried in air, produced a clear, flexible film.

EXAMPLE 5

Two hundred forty parts of Rohm & Haas N-495 acrylic emulsion were added to a reaction vessel as shown in the drawing and mixing of the emulsion was commenced. The air space above the surface of the acrylic emulsion was then filled with carbon dioxide gas at a pressure of 1 atmosphere. One hundred twenty parts of water were then added to the acrylic mix followed by the addition of 30 parts of the epoxy resin dispersion prepared in accordance with the method set forth in Example 1. After the addition of the epoxy resin to the acrylic mix was completed, 240 parts of Rohm & Haas AC-388 acrylic emulsion were added to the reaction vessel and mixing was continued. Upon completion of the addition of all of the reactants, the carbon dioxide gas flow was stopped and the mixing of the reaction vessel contents was continued for approximately 30 minutes. The resulting product had a pH of approximately 6 and, when applied to substrates and dried in air, provided a clear flexible coating.

EXAMPLE 6

Example 5 was repeated except that the epoxy resin dispersion of Example 3 was used in lieu of the epoxy resin dispersion used in Example 1. The resulting product had a pH of approximately 6.5 and, when applied to substrates and dried in air, provided a clear, flexible coating.

As will be appreciated by those skilled in the art, numerous organic solvents which are soluble with water and which are inert in the sense that they will not participate in or adversely affect the epoxy-acrylate reactions, may be employed in the preparation of the epoxy and acrylate premixes, as well as the aqueous dispersions of epoxide and acrylate which are to be combined in accordance with the invention. Examples of suitable materials which may be used are n-butanol, t-butanol, isopropyl alcohol, monobutyl glycol ether ("Cellosolve"), monobutyl glycol ether acetate ("Cellosolve" acetate) and toluene. Other suitable solvents will readily occur to those skilled in the art. In preparing the premixes and dispersions of resins to be combined in accordance with the invention, it is essential to select solvents which are compatible, i.e. miscible one with another, such that the liquid component of the premix, of the aqueous resin dispersion, and of the final epoxy derivative-acrylate mixture includes only one liquid phase.

The aqueous single liquid phase dispersions of the epoxy derivative-acrylate compositions prepared above are characterized by long shelf life, and a viscosity of between 10 and 15 centipoises. These dispersions may be applied to substrates by any suitable, well known technique, such as by brush, roller or airless spray. The application tools may be cleaned with water. The applied dispersion will air dry at temperatures above about 40° F. to provide strongly adherent, flexible coatings having thermoplastic memory characteristics. For example, the coatings of films obtained from the air-dried dispersion of the composition of the invention prepared in Example 1 above are characterized by the following:

odor - none color clear at dry film thicknesses up to about 8 mils adhesion - excellent adhesion to substrate of wood, metal, plaster, concrete, cement hardness - dries to touch in air at temperatures of from 45° F. to 100° F. within 15 minutes and can be over-coated after 20 minutes depending upon film thickness abrasion resistance - 270 coefficient ASTMD-658 elongation - greater than 30%.

It should be understood that while the present invention has been described in considerable detail with respect to certain specific embodiments thereof, it is not to be considered limited to those embodiments, but may be used in other ways without departure from the spirit of the invention or the scope of the appended claims.

What is claimed is:

1. The process for stabilizing the velocity of the primary reaction of an epoxide having at least one oxirane group in an aqueous system which comprises:
   passing said epoxide into a reaction zone including an aqueous liquid and carbon dioxide for generating resonance of the oxirane oxygen of said epoxide when it contacts said carbon dioxide,
   contacting said epoxide with said carbon dioxide to stabilize said epoxide by equalizing the reactivity rates of the alpha and beta carbon atoms of said oxirane group in the subsequent primary reaction of said epoxide in aqueous phase, and
   passing said stabilized epoxide into said aqueous liquid.

2. The process of claim 1 wherein said liquid includes a compound selected from the group consisting of monomers and polymers of alpha, beta unsaturated monovinylidene carboxylic acids and esters thereof reactive with said epoxide.

3. The process of claim 1 wherein said epoxy compound comprises the condensation product of an epihalohydrin and a polyol.

4. The process of claim 3 wherein said polyol is selected from the group consisting of dihydric phenols and polyhydric alcohols.

5. The process of claim 3 wherein said epoxy compound comprises the condensation product of epichlorohydrin and bis-(4-hydroxyphenyl)2,2 propane.

6. The process of claim 2 wherein said compound is a monomeric or polymeric ester of acrylic acid reactive with said epoxy compound.

7. The process of claim 6 wherein said acrylic acid is selected from the group consisting of acrylic and methacrylic acid.

8. The process for preparing an aqueous dispersion of a film-forming epoxy-acrylate mixture which comprises:
   introducing a polyepoxide including terminal epoxy groups into a reaction zone including a single phase aqeuous dispersion of an acrylic material reactive with said epoxide and selected from the group consisting of monomers and polymers of alpha, beta unsaturated monovinylidene carboxylic acids and esters thereof, the surface of which dispersion of said acrylic material is in contact with and which supports a layer of carbon dioxide maintained in said reaction zone and in contact with the surface of said dispersion at a pressure of at least 1 atmosphere,
   contacting said polyepoxide with said carbon dioxide,
   passing said polyepoxide from said carbon dioxide layer directly into said aqueous dispersion of said acrylic material to provide a mixture in which the weight ratio of epoxy solids to acrylic material solids is within the proportions 0.1:99.9 and 50:50, and
   stirring said mixture until addition of said polyepoxide thereto is complete to provide a stable, film-forming, single liquid phase dispersion of said polyepoxideacrylic mixture.

9. The process of claim 8 in which the temperature of said mixture is maintained at from 4° C. to 40° C.

10. The process of claim 8 wherein the weight ratio of epoxy solids to acrylic material solids in said mixture is in the proportion equal to or less than 1 to equal to or greater than 2.

11. The process of claim 8 wherein said epoxide is the condensation product of an epihalohydrin and a polyol.

12. The process of claim 11 wherein said polyol is selected from the group consisting of dihydric phenols and polyhydric alcohols.

13. The process of claim 11 wherein said polyepoxide comprises the condensation product of epichlorohydrin and bis-(4-hydroxyphenyl)2,2 propane.

14. The process of claim 8 wherein said acrylic material comprises an interpolymer of ethyl acrylate, methyl methacrylate and methacrylic acid.

15. The process of claim 8 wherein said polyepoxide comprises the condensation product of an epihalohydrin and a polyol selected from the group consisting of dihydric phenols and polyhydric alcohols, and said acrylic material comprises a polymerized alkyl ester of acrylic or methacrylic acid wherein the alkyl group includes from 1 to 4 carbon atoms.

16. The aqueous dispersion of stabilized epoxide prepared by the process of claim 1.

17. The aqueous dispersion of the mixture prepared by the process of claim 2.

18. The aqueous dispersion of the mixture prepared by the process of claim 7.

19. The stable, film-forming dispersion of the polyepoxideacrylic mixture prepared by the process of claim 8.

20. The stable, film-forming dispersion of the polyepoxideacrylic mixture prepared by the process of claim 14.

21. The stable, film-forming dispersion of the polyepoxideacrylic mixture prepared by the process of claim 15.

22. A process for producing a strongly adherent, flexible coating on an article which comprises applying to at least one surface of the article a coating of the composition of claim 19, and drying the coated article in the air in a temperature of above 40° F.

23. A process for producing a strongly adherent, flexible coating on an article which comprises applying to at least one surface of the article a coating of the composition of claim 21, and drying the coated article in air at a temperature of above 40° F.

24. The process which comprises:
   passing an epoxide having at least one oxirane group into a reaction zone including carbon dioxide,
   contacting said epoxide with said carbon dioxide in said reaction zone, and
   combining said epoxide with an aqueous liquid to provide an aqueous dispersion of said epoxide.

25. The process of claim 24 wherein said epoxy compound comprises the condensation product of an epihalohydrin and a polyol.

26. The process of claim 24 wherein said polyol is selected from the group consisting of dihydric phenols and polyhydric alcohols.

27. The process of claim 25 wherein said epoxy compound comprises the condensation product of epichlorohydrin and bis-(4-hydroxyphenyl)2,2 propane.

28. The process of claim 24 wherein said liquid includes a compound selected from the group consisting of monomers and polymers of alpha, beta unsaturated monovinylidene carboxylic acids and esters thereof reactive with said epoxide and further including the step of:
   combining said epoxide with said compound in said liquid to provide an aqueous dispersion of mixture of said epoxide and said compound.

29. The process of claim 28 wherein the compound comprises a monomeric or polymeric ester of an acrylic acid reactive with said epoxide.

30. The process of claim 29 wherein said acrylic acid is selected from the group consisting of acrylic acid and methacrylic acid.

31. The aqueous dispersion prepared by the process of claim 24.

32. The aqueous dispersion of the mixture prepared by the process of claim 28.

* * * * *

UNITED STATES PATENT OFFICE
CERTIFICATE OF CORRECTION

Patent No. 4,057,524    Dated November 8, 1977

Inventor(s) William R. Menyhert

It is certified that error appears in the above-identified patent and that said Letters Patent are hereby corrected as shown below:

Column 12, line 53, Claim 26, "claim 24" should be --claim 25--

Column 12, line 56, Claim 27, "claim 25" should be --claim 24--

Signed and Sealed this

Seventh Day of March 1978

[SEAL]

Attest:

RUTH C. MASON
Attesting Officer

LUTRELLE F. PARKER
Acting Commissioner of Patents and Trademarks